United States Patent
MacLaughlin

(10) Patent No.: US 9,930,764 B2
(45) Date of Patent: Mar. 27, 2018

(54) ARTICULATED X-RAY SUPPORT BOOM USING JAMMABLE MATERIAL

(71) Applicant: Carestream Health, Inc., Rochester, NY (US)

(72) Inventor: Scott T. MacLaughlin, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 96 days.

(21) Appl. No.: 15/068,902

(22) Filed: Mar. 14, 2016

(65) Prior Publication Data

US 2017/0265288 A1 Sep. 14, 2017

(51) Int. Cl.
*H05G 1/02* (2006.01)
*A61B 6/00* (2006.01)

(52) U.S. Cl.
CPC .............. *H05G 1/02* (2013.01); *A61B 6/4405* (2013.01); *A61B 6/4464* (2013.01)

(58) Field of Classification Search
CPC ....... A61B 6/4405; A61B 6/4464; H05G 1/02
See application file for complete search history.

(56) References Cited

U.S. PATENT DOCUMENTS

| 9,713,873 | B2* | 7/2017 | Cheng | A61B 1/00078 |
| 2014/0314976 | A1* | 10/2014 | Niiyama | F15B 15/103 428/34.3 |
| 2015/0141756 | A1* | 5/2015 | Cheng | A61B 1/00078 600/146 |
| 2016/0045174 | A1* | 2/2016 | Wendlandt | A61B 6/105 378/98 |

OTHER PUBLICATIONS

N. Cheng et al., "Design and Analysis of a Robust, Low-cost, Highly Articulated Manipulator Enabled by Jamming of Granular Media", Manuscript from Massachusetts Institute of Technology, 2011, pp. 1-6.

* cited by examiner

*Primary Examiner* — Mark R Gaworecki

(57) ABSTRACT

An x-ray head support boom has a number of tube segments coupled together in series. Each segment may be formed from a flexible membrane and encloses a jammable medium that transitions between a fluidic state and a rigid state in response to an applied force. Each segment is coupled to an actuator for application of the force. At least one cable is coupled to one or more tube segments to apply a tensile force to bend the series of tube segments.

20 Claims, 11 Drawing Sheets

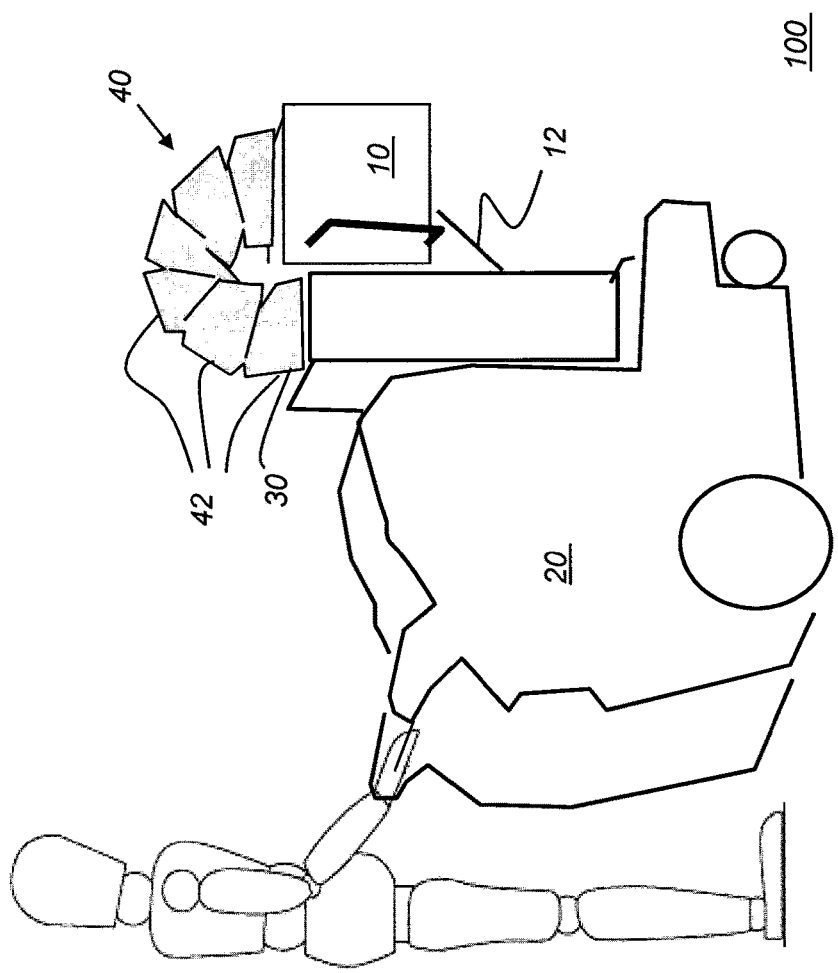

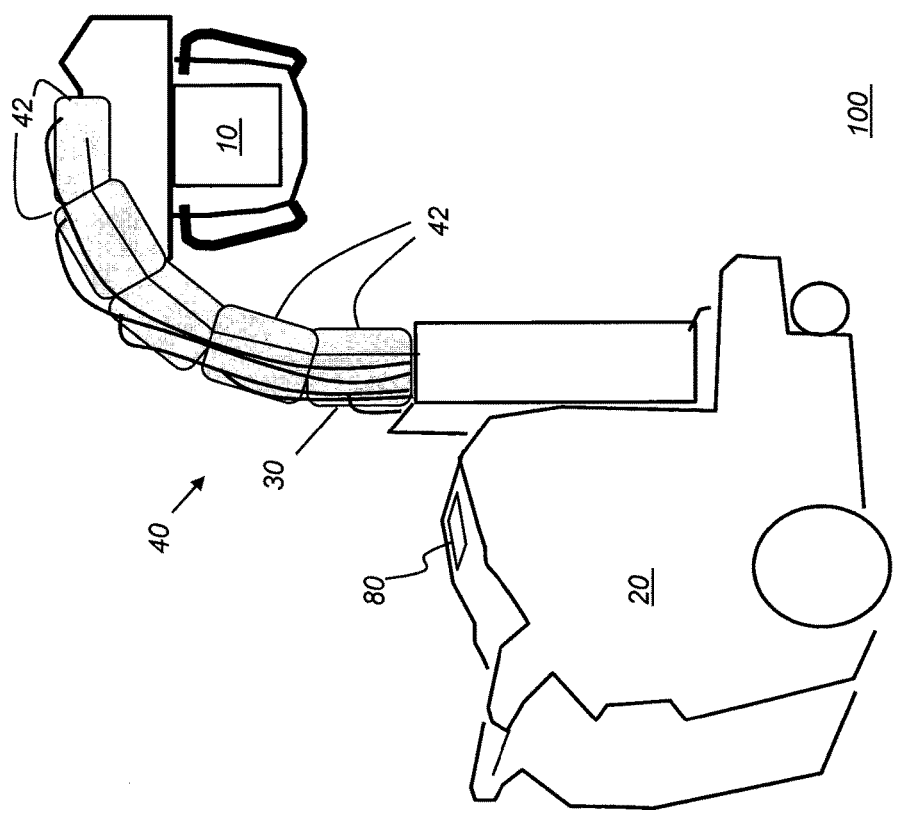

ARTICULATED X-RAY SUPPORT BOOM USING JAMMABLE MATERIAL

FIELD OF THE INVENTION

The present disclosure relates generally to radiographic imaging apparatus and more particularly to a support boom for an x-ray head.

BACKGROUND OF THE INVENTION

The x-ray head for a radiographic imaging apparatus is generally supported on some type of boom that allows the head to be properly positioned with respect to the subject being imaged and to the imaging detector. The x-ray head contains the emissive x-ray source and typically also has a number of related components that can include a collimator, controls, and guiding handles, for example. X-ray boom design is complicated by a number of factors, including the combined weight of the x-ray source and supporting components, the need to be able to flexibly position the head with the necessary rotational and translational degrees of freedom, and the requirement that the head position be stably maintained during setup and imaging procedures.

Supporting the boom for the x-ray head presents a particular challenge for mobile x-ray apparatus. Unlike conventional wall- and ceiling-mounted x-ray systems, mobile x-ray apparatus can be wheeled around the ICU or other area and brought directly to the patient's bedside. In these circumstances, the operating space for maneuvering the boom and x-ray head (for example, within the narrow space between patient beds) restricts the clinician's ability to quickly and accurately position the device for x-ray acquisition. In addition, the added weight and complexity of the head support boom and its associated hardware are factors that can add to the cost of these devices and complicate their operation and maintenance requirements. For example, where the x-ray head is mounted with a cantilevered arrangement, sufficient counterbalance mechanisms and ballast are required in the mobile x-ray cart base to allow movement by the clinician or technician. This tends to increase the overall weight of the mobile x-ray apparatus, thereby requiring more complex automated drive and steering mechanisms. These requirements, in turn, tend to increase product cost and complexity, with added risk factors related to unintended system motion.

Mobile apparatus designs in commercial use are characterized by complex, cantilevered boom designs with fixed or collapsible columns and the need for substantial counterweights, numerous supporting actuators, and fixed movement paths between spatial locations, often constrained by the mechanical design of boom components.

One concern that must be addressed in design of the support member relates to ease of positioning of the x-ray source mounted on its boom. For ease of operation under varying conditions, the technician should be able to easily position and orient the x-ray source without requiring both hands, without the need of additional tools, and without needing help from nearby personnel. This includes moving the x-ray source from its docked position used in transport to an imaging position. The mechanical problem of providing ease of positioning is complicated by the weight of the x-ray source and by its extension outward from the vertical axis.

Thus, there is a need for an x-ray head support boom that offers reduced weight, reduced parts count, and relative ease of use by the attending technician, particularly in confined areas, both for stationary x-ray systems and mobile x-ray apparatus.

SUMMARY OF THE INVENTION

An object of the present invention is to advance the art of radiography. A related object of the present invention is to address the need for a mobile radiography unit that allows ease of movement of the boom assembly between various positions.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

From one aspect, the present invention provides an x-ray head support boom comprising a plurality of tube segments, coupled together in series, each segment formed from a flexible membrane and enclosing a jammable medium that transitions between a fluidic state and a rigid state in response to an applied force, each segment coupled to an actuator for application of the force that changes the jammable medium between states, at least one cable coupled to one or more tube segments, and a first motor applying a tensile force to the at least one cable wherein the tensile force bends the one or more tube segments.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 1A is a perspective view of a mobile radiography apparatus having an articulated x-ray head support boom using jammable material, with the boom in a relaxed state.

FIG. 1B is a perspective view of a mobile radiography apparatus having an articulated x-ray head support boom using jammable material, with the boom in a rigid state and having an arcuate shape.

DETAILED DESCRIPTION OF THE INVENTION

Figure 1C:
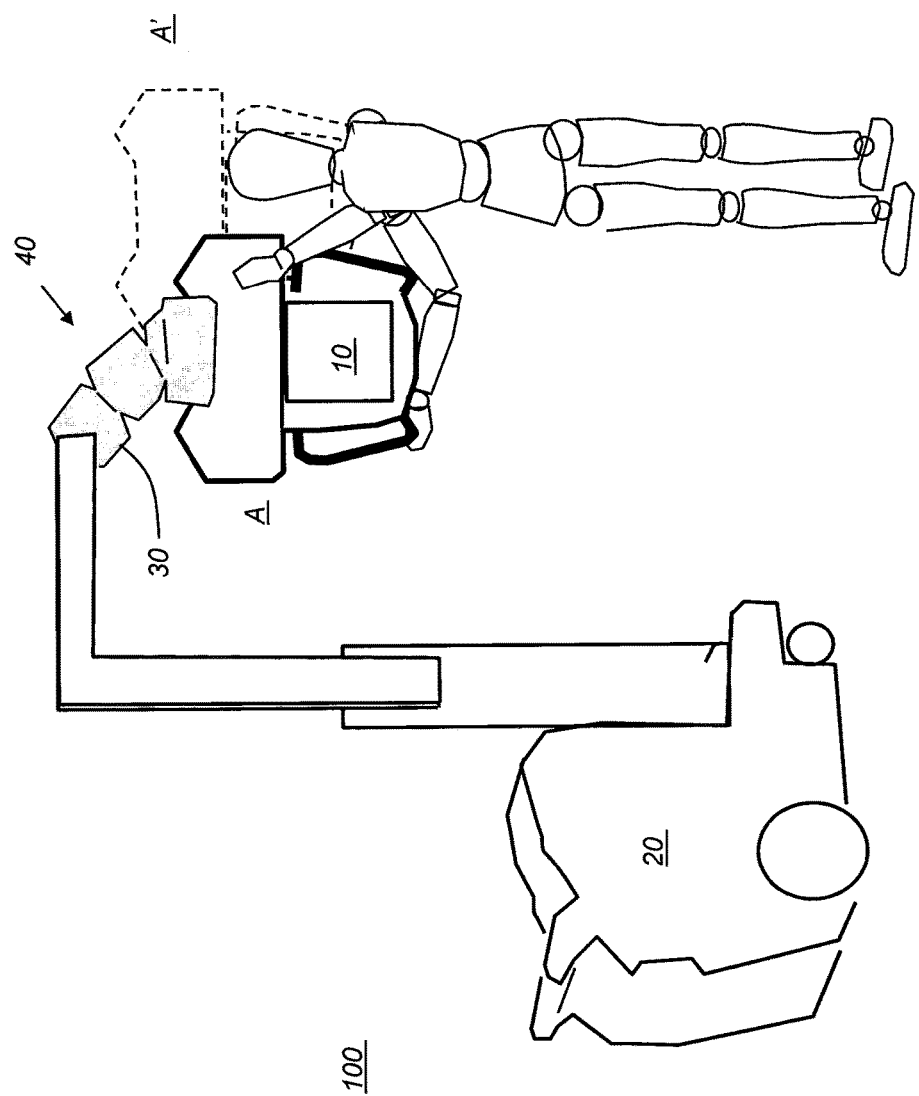
FIG. 1C is a perspective view of a mobile radiography apparatus having an articulated x-ray head support boom using jammable material, with the boom in a rigid state and having a linear shape.

The following is a detailed description of the preferred embodiments of the disclosure, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another.

Apparatus and methods of the present disclosure address the need for an x-ray head support boom that articulates to allow flexible positioning of an x-ray head. The x-ray head support boom of the present disclosure can be particularly suitable for a mobile radiography apparatus, but can similarly be used with a stationary x-ray system, such as a wall-mounted or ceiling-mounted system. The support boom can also be used for support of a C-arm or other mount that supports the x-ray head and related components.

The perspective views of FIGS. 1A, 1B, and 1C show a mobile radiography apparatus 100 that has a movable cart 20 that can be wheeled from one location to another, such as within an intensive care unit (ICU) or other department or facility. An x-ray head 10 is coupled to the end of a flexible tube 30 that provides at least a portion of an articulated x-ray head support boom 40 for positioning x-ray head 10 for imaging. FIG. 1A shows boom 40 in a flexible or contracted configuration. X-ray head 10 can be seated on a shelf or bracket 12 of cart 20, such as for ease of transport between use sites. FIG. 1B shows boom 40 in an extended, rigid configuration for imaging use.

FIG. 1C shows boom 40 as an articulated structure allowing head 10 movement between two locations, shown as A and A' in this example. In the FIG. 1C embodiment, articulated boom 40 uses both a rigid metal boom and flexible boom portions.

Figure 2:
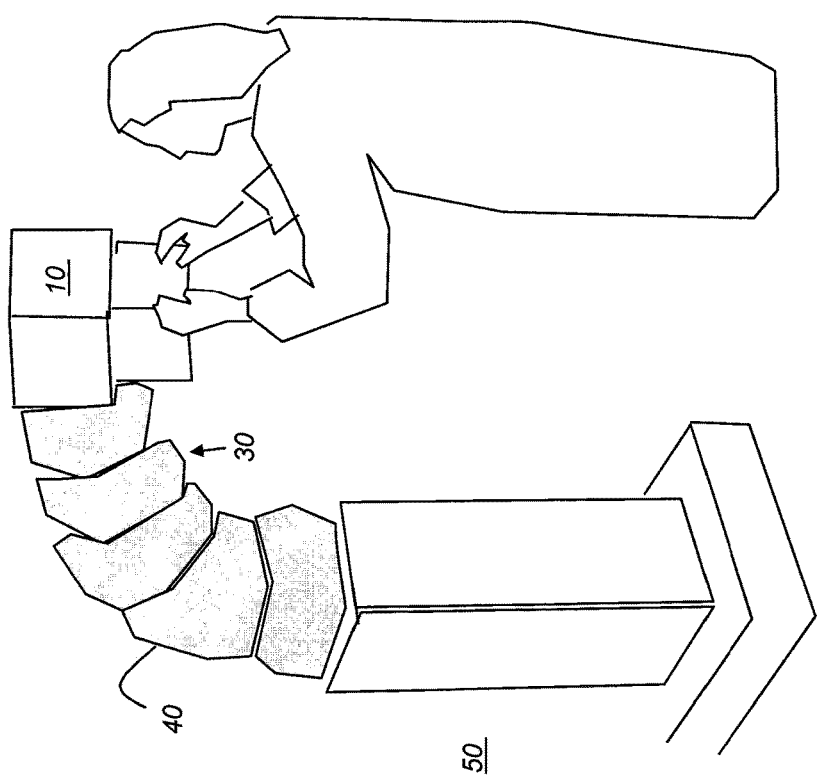
FIG. 2 is a perspective view of a stationary radiography apparatus having an articulated x-ray head support boom using jammable material, with the boom in a rigid state and having an arcuate shape.

The perspective view of FIG. 2 shows a stationary x-ray apparatus 50 that has an articulated support boom 40 using tube 30 to allow adjustable x-ray head 10 positioning.

Figure 3:
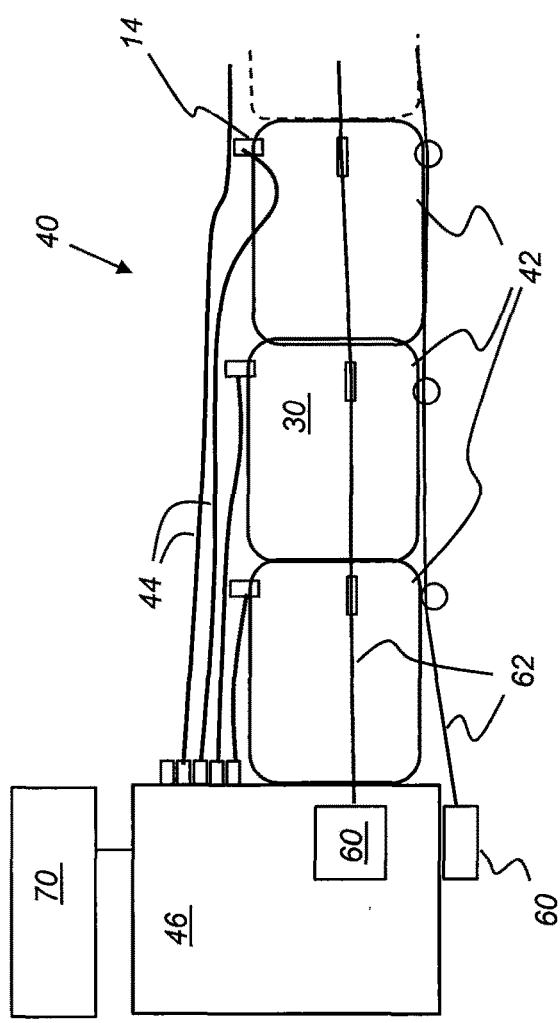
FIG. 3 is a schematic view that shows components of an exemplary support boom that extends horizontally.

The schematic view of FIG. 3 shows components not shown in previous figures for providing an exemplary support boom 40 that extends horizontally. Support boom 40 is formed as a tube 30 from a number of modular tube segments 42, coupled together in series. Each tube segment 42 is formed from a flexible medium, such as a plastic or other flexible material. According to an embodiment, the material that is used is impermeable to gas or liquid, so that segment 42 is capable of maintaining an internal pressure or vacuum that, in turn, controls a variable rigidity for each segment 42. Each segment 42 has a corresponding pressure control conduit 44 connected to a pump 46 that provides a vacuum or pressure source through a valve 14 that serves as an actuator for movement of air or other gas or liquid used as a force for the jamming mechanism that provides rigidity of the jamming medium as described in more detail subsequently.

Still referring to FIG. 3, one or more cables 62, each driven from a motor 60, are provided for providing tensile force along a direction. The applied urging force of a cable 62 can cause corresponding motion of one or more segments 42. The urging force of cable 62 can also bend the boom 40 by imparting a variable arcuate shape to the tube 30. The combination of variable rigidity and cable actuation and tension allows support boom 40 to assume a given shape or curvature and rigidity for urging movement between positions and supporting x-ray head 10 once it is in position. A control logic processor 70, such as a computer or a microprocessor or other dedicated processor, in signal communication with motor and actuator components and an optional display, can be used to control boom operation. Similar components can be used for a boom that extends vertically.

Figure 4B:
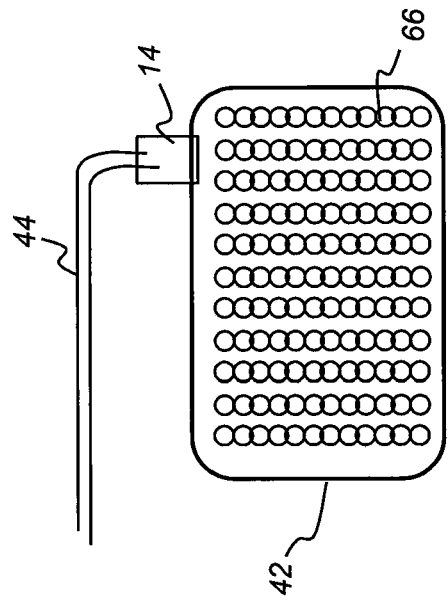
FIG. 4B is a schematic cross-sectional view that shows a tube segment with jammable material in a rigid state.
Figure 4A:
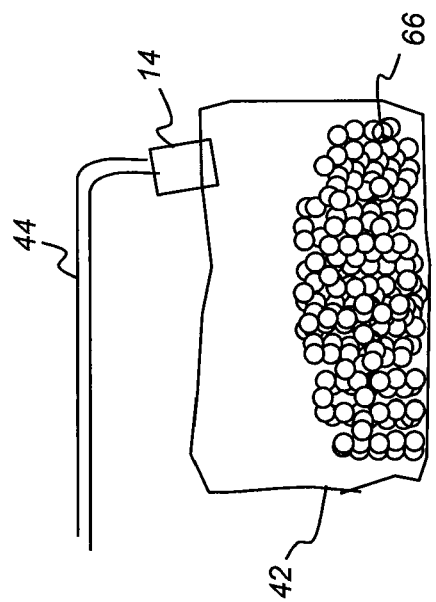
FIG. 4A is a schematic cross-sectional view that shows a tube segment with jammable material in a relaxed state.

FIGS. 4A and 4B are schematic diagrams that show how variable rigidity for each tube segment 42 of boom 40 can be controlled. As FIG. 4A shows, each segment 42, formed from a flexible membrane, acts as a pressurizable envelope containing a jammable granular medium 66. Granular medium 66 is termed "jammable" because it effects a mechanical phase change with a change in atmospheric pressure or other applied force, such as liquid flow velocity or vibration, at levels beyond a given threshold.

According to an embodiment of the present disclosure, vacuum is used as the applied force to stiffen granular medium 66. FIG. 4B shows medium 66 in its jammed state, with vacuum force applied to segment 42. In this state, granular medium 66 aligns or is otherwise arranged to transform the stiffness of segment 42 from a more flaccid, non-rigid, or relaxed state shown in FIG. 4A to the rigid state shown in FIG. 4B. By controlling the amount of vacuum, pump 46 of FIG. 3 can control the individual rigidity of each segment 42 of boom 40. This not only allows boom 40 to have a variable length of extension within a range, it also allows boom 40 to have various shapes in the stiffened state, such as the arcuate shape shown in FIG. 1B and FIG. 2, or the relatively linear shape shown in FIG. 1C and FIG. 3.

Individual segments 42 can be configured to be extendable and contractible in a telescoping configuration. Individual segments 42 used to form tube 30 can be of different diameters and lengths, depending on support requirements. Thus, for example, boom 40 can be thicker near its base and be tapered to have reduced diameter near the x-ray head 10. Segments 42 can also have pre-set bends if needed, such as to condition the tube 30 for bending to particular storage or positioning configurations.

An alternative method of actuation applies positive pressure to the various segments in order to enable boom movement between head positions. In this method, the granular medium is jammed (i.e. compressed) in the free state (that is, with no external pressure applied). Positive pressure expands the volume of the flexible membrane segment(s) thereby reducing the friction of the jamming medium. This method would provide a fail-safe method of operation should the system lose power or pressure. In this instance, the un-actuated system would "lock" in its current configuration, retaining the x-ray head at its current position. This would prevent unintended motion that could otherwise present a hazardous condition for the technician, patient, or nearby persons.

Segments 42 can be formed in a number of ways. According to an embodiment, individual segments 42 are fabricated from suitable materials, fitted with valve actuator and jammable media contents, then joined together serially to provide boom 40. Segments 42 may be sewn together or otherwise fastened together, for example. Jammable media materials may be provided within one or more channels, individual pockets, or smaller envelopes within segment 42, or may be used to at least partially fill a single large cavity.

Segments 42 can optionally include stiffeners, such as internal or external coils for retaining some amount of stiffness when the jammable medium is in the un-jammed, relaxed, or flaccid state.

Figure 5A:
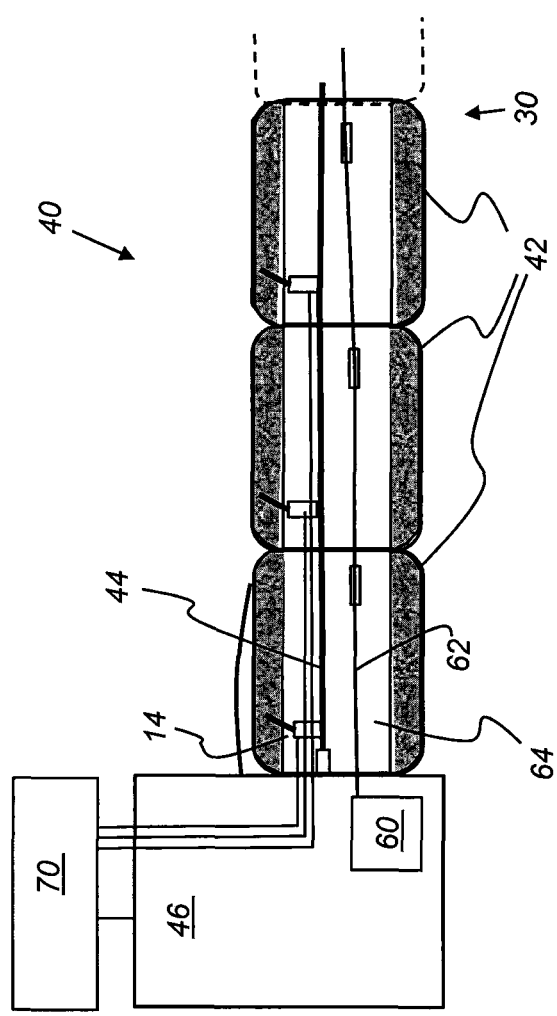
FIG. 5A is a cross-sectional view of a portion of a support boom that has internal tubing and cable actuation within a hollow annulus.
Figure 5B:
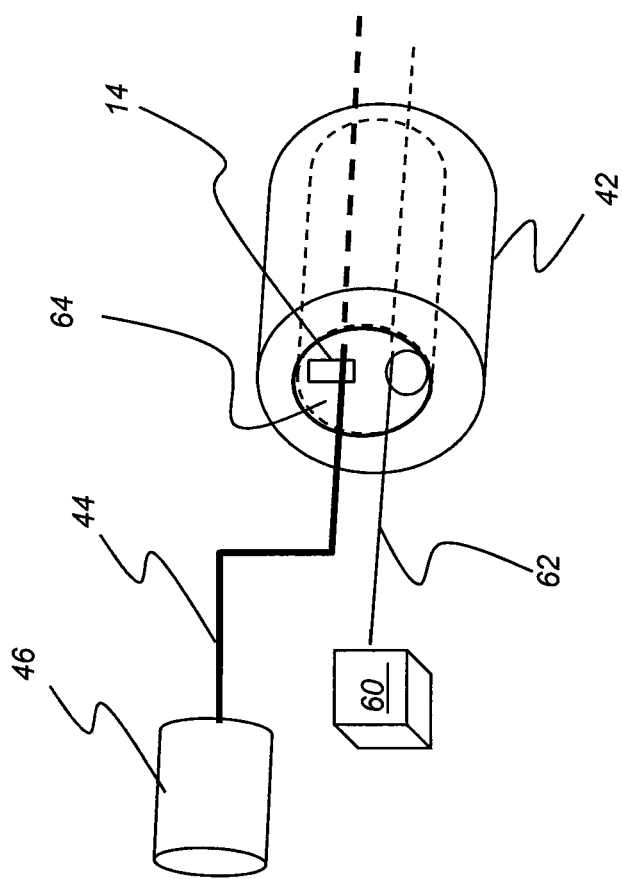
FIG. 5B shows a schematic diagram of a single tubing segment 42 from a perspective view

FIG. 5A is a cross-sectional view of a portion of a support boom that has internal tubing and cable actuation routed to the individual tubing segments 42 within a hollow annulus that provides an internal channel 64. FIG. 5B shows a schematic diagram of a single tubing segment 42 from a perspective view. Conduit 44 extends through channel 64 and directs air or other fluid into, or out from, the medium 66 to change between more rigid and more relaxed or fluidic states as described with reference to FIGS. 4A and 4B. A valve 14 within channel 64 is actuated between open and closed positions according to signals from control logic processor 70. Cable 62 extends from motor 60 to each segment 42 through the channel provided by internal channel 64.

Jammable or Stiffness Phase-Change Materials

Embodiments of the present disclosure use a boom that is configured to adopt a particular shape and position by using a reversible process that employs jammable media. A jammable medium changes from a fluidic state to a rigid state in response to an applied force or stimulus.

Various types of reversibly jammable materials have been used for conformable manipulators and other devices. These materials are also termed phase change materials or stiffness phase change materials because they change from a loose, fluidic state under one set of conditions, then become stiff or rigid under a different set of conditions. Jammable granular materials suited for use under variable vacuum levels include hollow and solid glass beads of given dimensions, ground coffee, diatomaceous earth, and sawdust, for example. Each of these types of granular materials enables the reversible process for variable rigidity or fluidity according to vacuum level.

Other types of stiffness phase change materials can be used, including materials that provide a reversible stiffness under different conditions. A material that jams when pressure is applied or due to changes in fluid flow conditions can be used, for example. According to an alternate embodiment of the present disclosure, behavior that is opposite to that described with reference to FIGS. 4A and 4B is used. Jammable material is packed tightly within a segment 42 envelope so that the segment is rigid under ambient pressure conditions. To reduce stiffness for boom movement, pressure is applied to the segment; this applied force effectively increases the volume of the jammed envelope. As a result of increased air pressure, or other fluid pressure, the jammed material is momentarily un-jammed, reducing rigidity to allow movement. A material that is jammed under normal atmospheric pressure but un-jams when pressure exceeds a threshold can alternately be used.

Still other approaches use different force mechanisms to effect a reversible jamming response. One mechanism uses dilatants that exhibit a variable viscosity that increases with the rate of shear. A dilatant (also called shear thickening) material is one in which viscosity increases with the rate of shear. The dilatant effect is believed to occur when closely-packed particles are combined with enough liquid to fill the gaps between them. At low velocities, the liquid acts as a lubricant, and the dilatant flows easily. With the liquid forced through the medium at higher velocities, the liquid is unable to fill the gaps created between particles, and friction greatly increases, causing an increase in viscosity.

One such dilatant material is a combination of cornstarch and water, that can be made to stiffen in response to vibration. A piezoelectric motor or other vibration source can be used as an actuator to provide the needed force for changing material rigidity.

Other materials that, while not truly phase change materials, can be contemplated for use for a support boom using variable stiffness can include electrorheological (ER) fluids and magnetorheological (MR) fluids. ER fluids are suspensions of extremely fine non-conducting particles (up to, for example, 50 micrometers in diameter) in an electrically insulating fluid. The apparent viscosity of these fluids can change reversibly by an order of up to 100,000 in response to an electrical field. An MR fluid is a suspension of micrometer-sized magnetic particles in a carrier fluid, usually a type of oil. When subjected to a magnetic field, the fluid greatly increases its viscosity, to the point of becoming a viscoelastic solid. The yield stress of the fluid when in its active (on) state can be controlled very accurately by varying the magnetic field intensity.

It should be noted that the jammable material may or may not have intermediate states of progressively increasing rigidity. Pressure or vacuum above or below a particular threshold, for example, may lock media granules into position or free them from an ordered arrangement in a binary manner, so that the jammable material is either highly rigid or substantially fluidic. For other materials, rigidity can be proportional to the jamming or un-jamming force that is applied.

Positioning Options

Embodiments of x-ray head support boom 40 allow the technician to position the x-ray head in a flexible manner, adjusting and relaxing boom stiffness as needed by adjustable rigidity of segments 42 and allowing tube 30 to have various arcuate shapes for obtaining the desired position.

Using the boom of the present disclosure, articulated support boom 40 can be used to position x-ray head in a number of ways. Manual positioning of x-ray head 10 can be performed by the technician by an instruction or movement that causes x-ray system logic to sense repositioning movement by the technician and to respond by releasing and applying variable stiffness or rigidity to various segments in order to achieve a given position.

Figure 6:
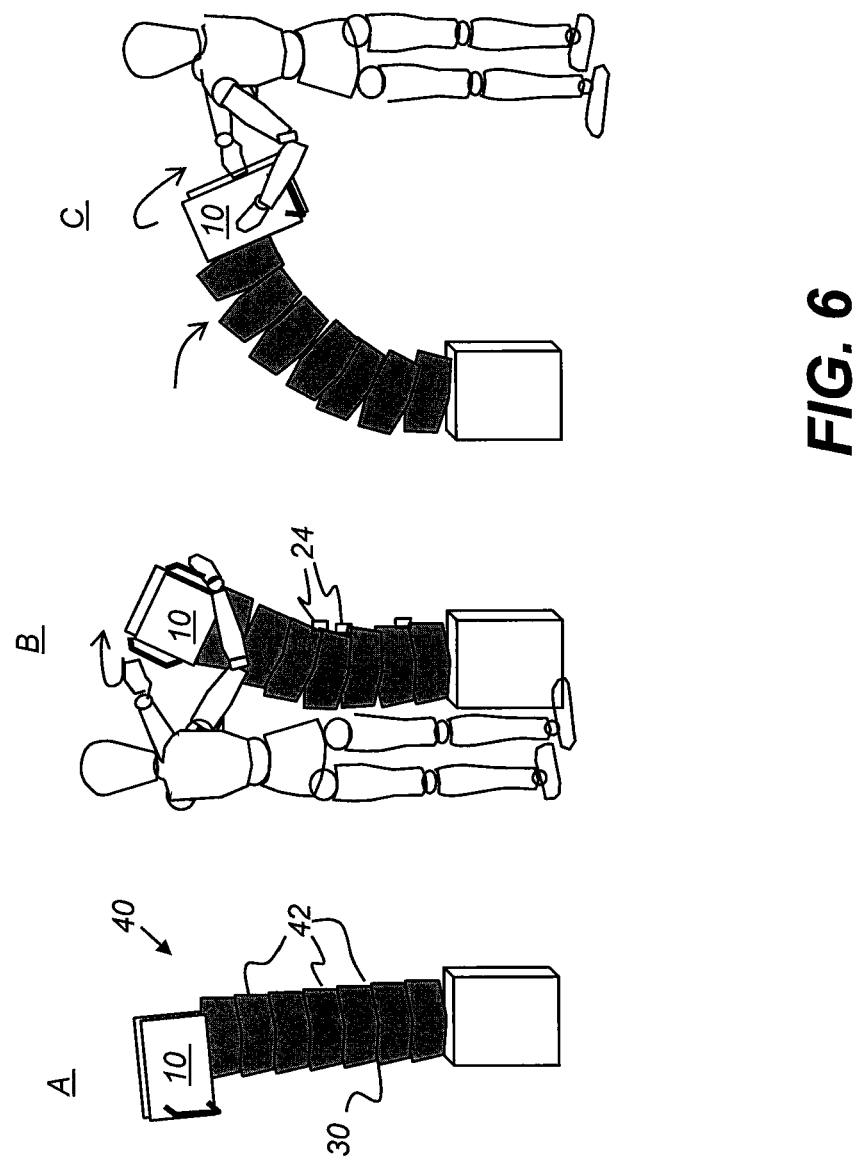
FIG. 6 is a perspective diagram showing movement to adjust x-ray head position using a boom of the present disclosure.

FIG. 6 shows, in schematic form, how support boom 40 can be moved by a technician from one position to another. Positions in this incremental movement sequence are labeled A, B, and C in this figure. The technician provides some type of instruction that energizes boom 40 for movement, such as by entering a keyboard command on a control console or by command entry at x-ray head 10, for example. Feedback sensing, using one or more sensors 24, can detect pushing or pulling force exerted by the technician in order to change boom 40 position. In a coordinated sequence, executed by control logic processor 70 (FIGS. 3 and 5A), individual segments 42 are adjusted to provide various levels of rigidity during movement, allowing head 10 to be turned and re-oriented. Rigidity changes can be momentary, allowing enough time for incremental shifting and adjustment of boom orientation and curvature as well as head 10 position. Full rigidity is restored at different points in the movement cycle, allowing support of the x-ray head 10 weight as the head 10 is moved from one position to another.

Figure 7:
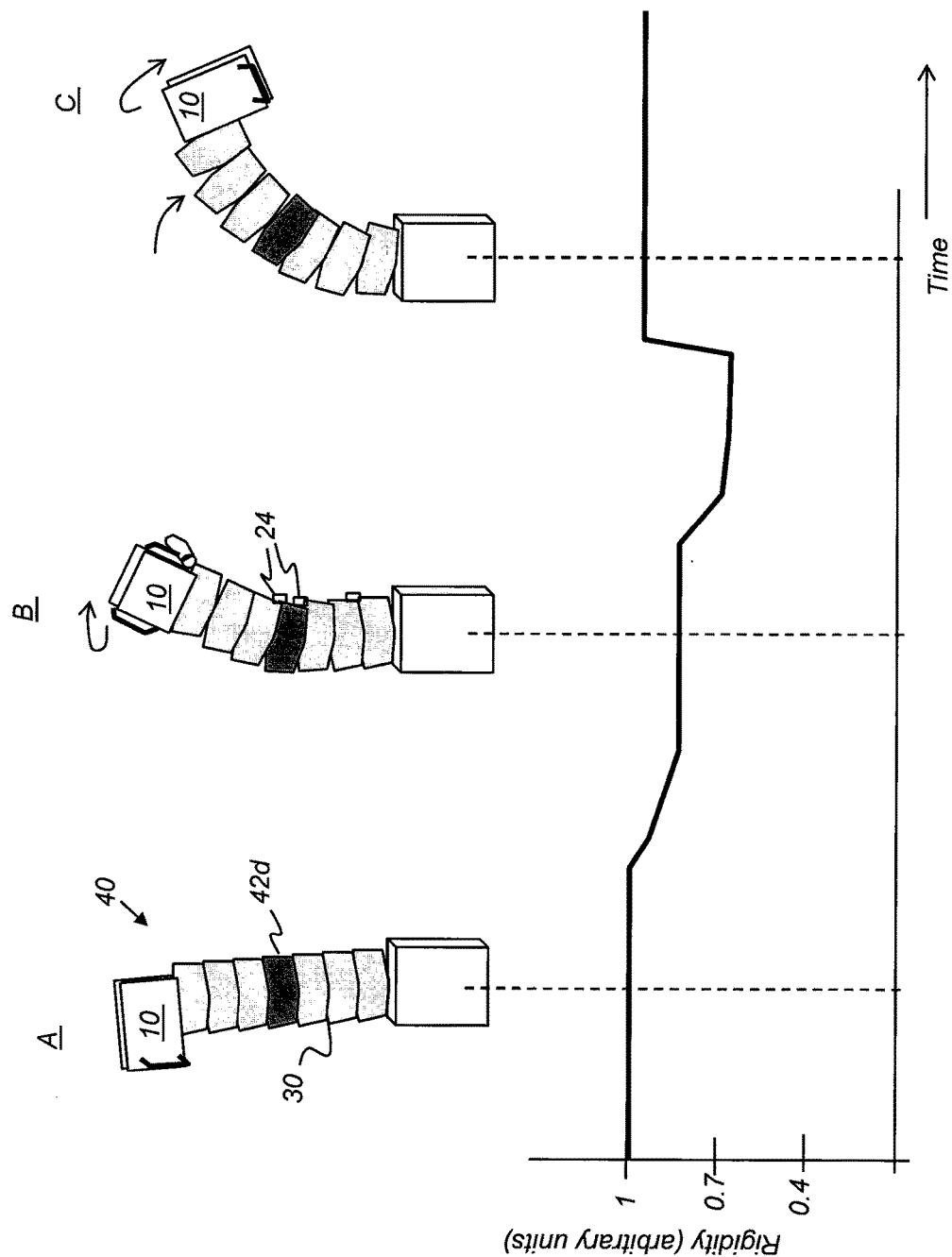
FIG. 7 is an exemplary timing diagram showing variable rigidity for one segment of the x-ray support boom for the movement example of FIG. 6.

FIG. 7 is an exemplary timing diagram showing variable rigidity for one segment 42d of the x-ray support boom 40 for the movement sequence shown in FIG. 6. Rigidity for a segment is represented on a scale from 0 to 1 with higher rigidity assigned higher values. Fully rigid in the A position, a momentary drop in rigidity for segment 42d is needed in order to transition toward the B position. For continued movement to the C position, rigidity of segment 42*d* must be relaxed even further, until the desired position is achieved. Once movement is completed, segment 42*d* is returned to a fully rigid state. It should be noted that adjustment changes are also applied for the other segments 42 in boom 40, with timing and rigidity differences as needed to support the movement sequence. Sensors 24 are arranged along boom 40 in order to detect characteristics such as angular orientation, pressure, proximity, and other parameters that indicate how the rigidity for individual segments 42 must be adjusted.

Figure 8:
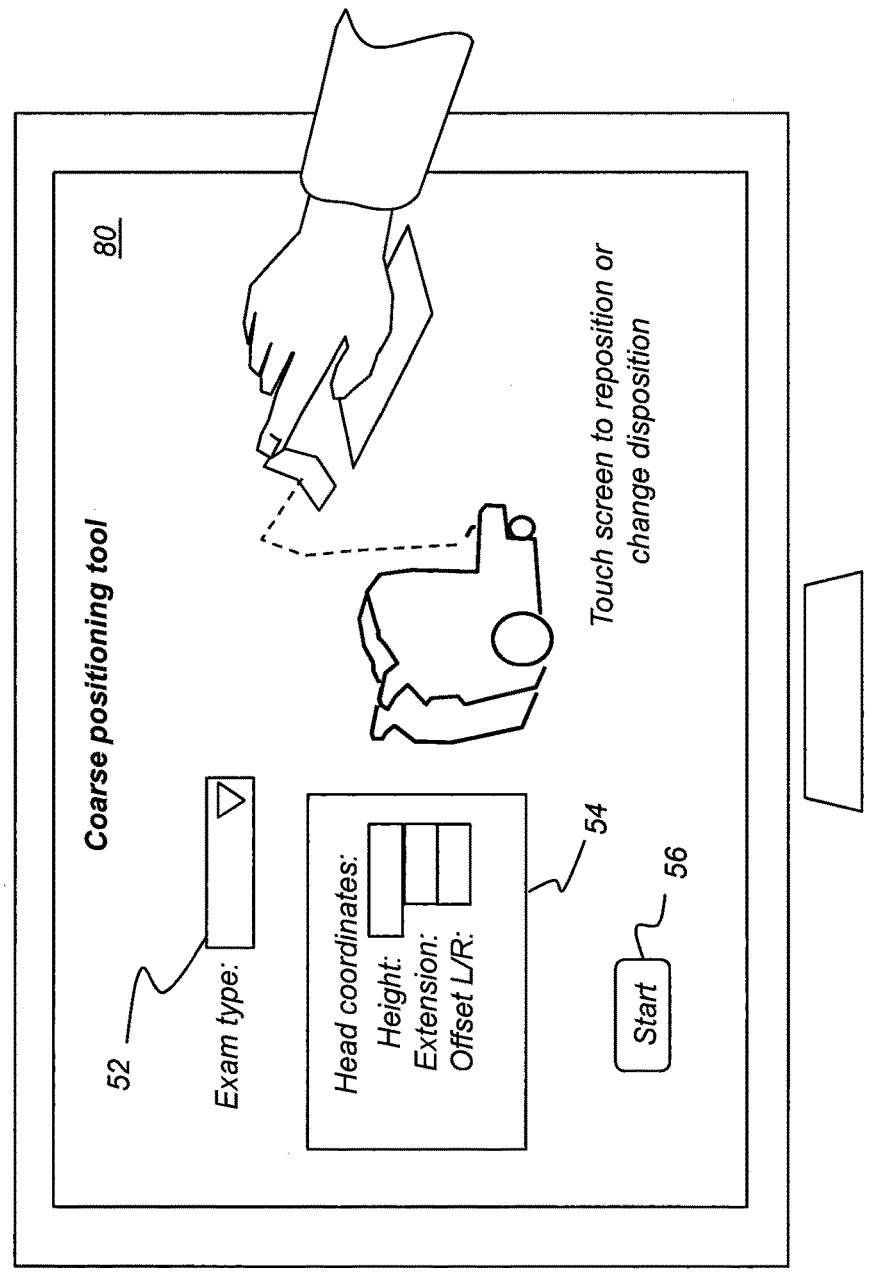
FIG. 8 is a plan view of an operator interface for a coarse positioning tool for an articulated x-ray boom according to an embodiment of the present disclosure.

Automated coarse positioning of boom 40 can also be provided. Referring to FIG. 8, there is shown a control screen display 80 for coarse positioning of the x-ray head support boom. Display 80 with this function may be provided as part of cart 20, as shown in FIG. 1B. The technician enters or selects an examination type, such as from a menu 52, and provides information on the patient disposition (prone, standing) and other data for initial positioning in a data entry section 54, then presses the Start instruction 56. Alternately, a touch screen interface is used to position an icon of the head at the approximate position. The touch screen interface can present 3-dimensional (3-D) images of the cart 20 or boom 40 structures, enabling coarse positioning of the x-ray head 10 with 3-D manipulation. During or after screen positioning, the technician can then lift the head from a resting position, or from its current position, and use the coarse positioning instructions to assist in positioning the x-ray head. As the head is moved by the technician, sensing components of the radiography apparatus correspondingly adjust and relax the rigidity of different segments 42 in order to support continuous boom 40 movement from one point to another.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention.

What is claimed is:

1. An x-ray head support boom comprising:
   an actuator coupled to a source of fluid pressure;
   a plurality of tube segments coupled together in series and coupled to the actuator, each of the tube segments formed from a flexible membrane enclosing a jammable medium that is compressed and rigid in an ambient pressure state and which is configured to transition to a fluidic and flexible state in response to the actuator applying positive pressure to the jammable medium from the source of fluid pressure;
   at least one cable coupled to one or more of the tube segments; and
   a first motor to apply a tensile force to the at least one cable wherein the tensile force bends the series of tube segments.

2. The support boom of claim 1, wherein the actuator comprises a valve coupled to a conduit containing pressurized air or liquid.

3. The support boom of claim 1, wherein the actuator comprises a second motor for providing the applied fluid pressure.

4. The support boom of claim 1, wherein the actuator comprises a piezoelectric motor for providing the applied fluid pressure.

5. The support boom of claim 1, wherein one or more of the tube segments comprise an internal stiffener for maintaining a shape of the tube segment when the medium is in the fluidic state.

6. The support boom of claim 1, wherein the actuator comprises a pump for providing the applied fluid pressure through one or more conduits.

7. The support boom of claim 1, further comprising a control logic processor to control actuation of the support boom.

8. The support boom of claim 7, further comprising a display in signal communication with the control logic processor, the display configured to accept operator commands to control coarse positioning of the boom.

9. The support boom of claim 1, wherein the at least one cable extends through a channel internal to one or more of the tube segments.

10. An x-ray head support boom comprising:
    a tube made from a flexible membrane;
    an x-ray source secured to and supported by the tube;
    granular media contained within the flexible membrane; and
    a pressure source connected to the tube to selectively transition the granular media between a flexible fluid state when the pressure source is powered on and a rigid solid state when the pressure source is powered off.

11. The x-ray head support boom of claim 10, wherein the boom is attached to a mobile x-ray cart, and wherein the pressure source is powered off to allow the boom to be seated on the mobile x-ray cart during wheeled transport of the mobile x-ray cart.

12. The x-ray head support boom of claim 10, wherein the boom is attached to a wall or ceiling of a radiographic imaging room.

13. The x-ray head support boom of claim 10, wherein the tube comprises individual segments, and wherein each individual segment is selectively transitionable between the fluid and rigid states.

14. The x-ray head support boom of claim 13, wherein the individual segments are configured to be extendable and contractible in a telescoping configuration.

15. The x-ray head support boom of claim 13, wherein one or more of the segments comprises a stiffener to retain segment shape when the media therein is in the fluid state.

16. The x-ray head support boom of claim 13, wherein the flexible membrane for one or more of the segments comprises a material impermeable to fluid.

17. The x-ray head support boom of claim 10, wherein the pressure source is configured to continuously adjust a positive pressure applied to the tube such that the granular media is adjustable to varying degrees between the flexible fluid state and the solid rigid state corresponding to the applied positive pressure.

18. The x-ray head support boom of claim 10, further comprising at least one cable connected to an actuator for providing tensile force for bending the boom.

19. The x-ray head support boom of claim 10, further comprising one or more sensors that provide signals indicative of a position of the x-ray source.

20. A method for supporting an x-ray head, the method comprising:
    providing a boom having a plurality of coupled tube segments each formed from a flexible membrane and enclosing a jammable medium that transitions from a compressed rigid state to a flexible fluidic state response to activating an applied positive pressure;

accepting one or more operator instructions that are entered on a display monitor, the instructions indicating a desired position of the x-ray head;
sensing a position of the boom;
applying the positive pressure to one or more of the tube segments in accordance with the operator instructions;
applying a tensile force to the one or more of the tube segments to bend the boom to the desired position; and
locking the desired position of the boom by transitioning the jammable medium to the rigid state by deactivating the applied positive pressure.

\* \* \* \* \*